United States Patent [19]

Link

[11] Patent Number: 4,587,974
[45] Date of Patent: May 13, 1986

[54] LINEAR PRESSURIZING AND DEPRESSURIZING DEVICE

[75] Inventor: William T. Link, Berkeley, Calif.

[73] Assignee: Norse Instruments, Hayward, Calif.

[21] Appl. No.: 670,213

[22] Filed: Nov. 13, 1984

[51] Int. Cl.$^4$ .............................................. A61B 5/02
[52] U.S. Cl. .................................. 128/685; 128/677; 137/505
[58] Field of Search ............... 128/672, 677, 680–683, 128/685, 686; 137/505, 505.11, 505.2, 505.21

[56] References Cited

U.S. PATENT DOCUMENTS

| | | | |
|---|---|---|---|
| 4,178,918 | 12/1979 | Cornwell | 128/682 |
| 4,290,434 | 9/1981 | Jewett | 128/680 |
| 4,360,029 | 11/1982 | Ramsey, III | 128/681 |
| 4,367,751 | 1/1983 | Link et al. | 128/681 X |

FOREIGN PATENT DOCUMENTS 2060175  4/1981  United Kingdom .................... 681/

Primary Examiner—Kyle L. Howell
Assistant Examiner—Angela D. Sykes
Attorney, Agent, or Firm—Flehr, Hohbach, Test, Albritton & Herbert

[57] ABSTRACT

Devices for and methods of pressurizing or depressurizing a particular pressurizable container or housing in a substantially linear, fixed manner independent of the pressurized volume of the container are disclosed herein. These devices are especially suitable in an arrangement for taking blood pressure in which a cuff wrapped around a body part of a patient is pressurized or alternatively depressurized to detect the patient's systolic and diastolic pressures. The device acts on the cuff so that the latter is pressurized or depressurized in a substantially linear, fixed manner independent of the pressurized volume of the cuff, that is, independent of the size of the cuff.

12 Claims, 9 Drawing Figures

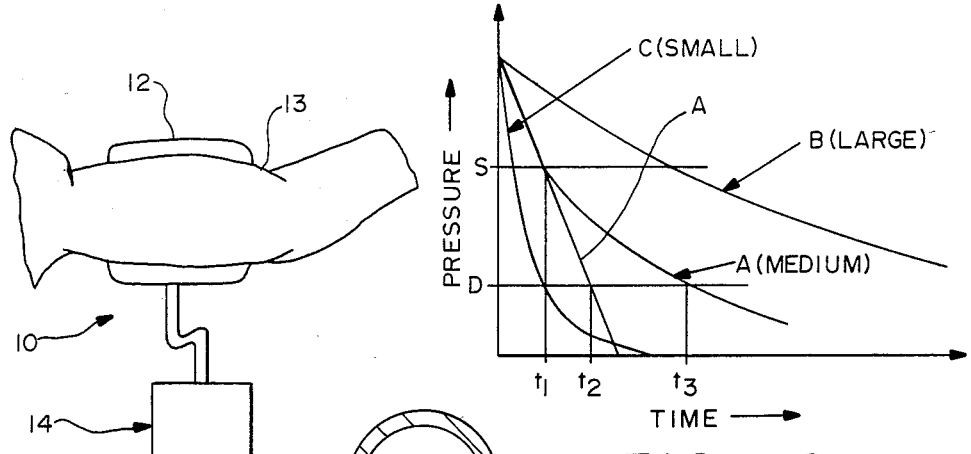
FIG.—1
FIG.—2
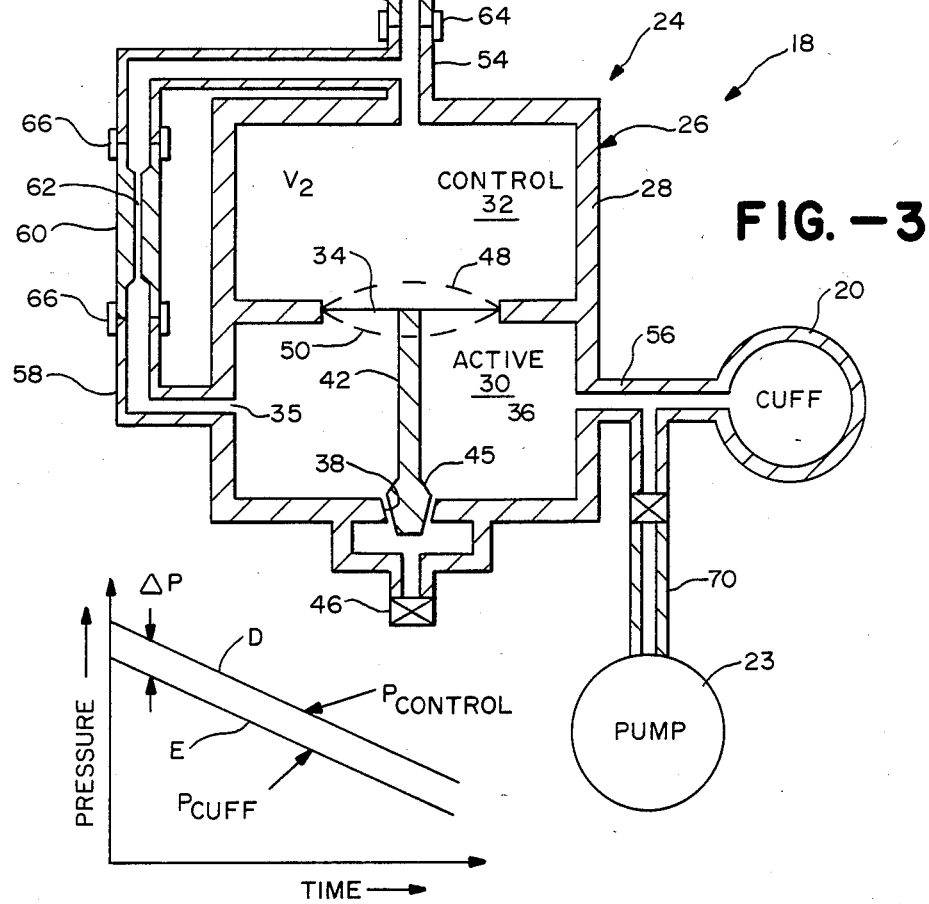
FIG.—3
FIG.—4

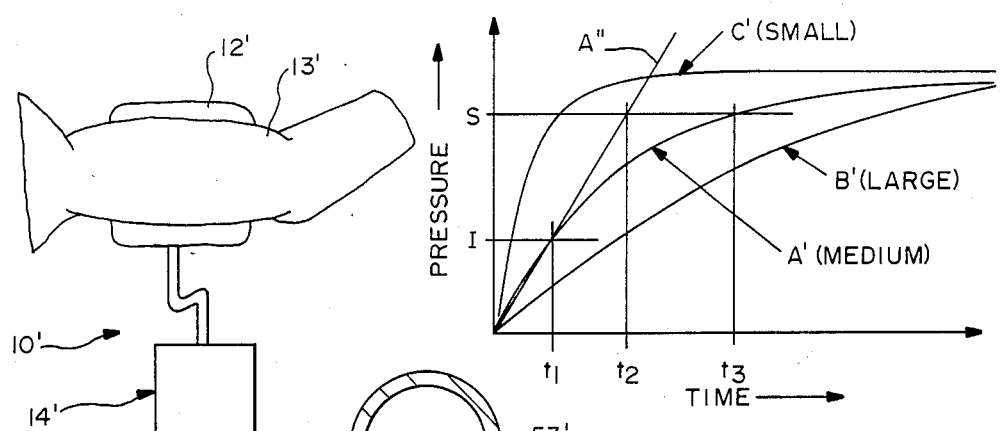
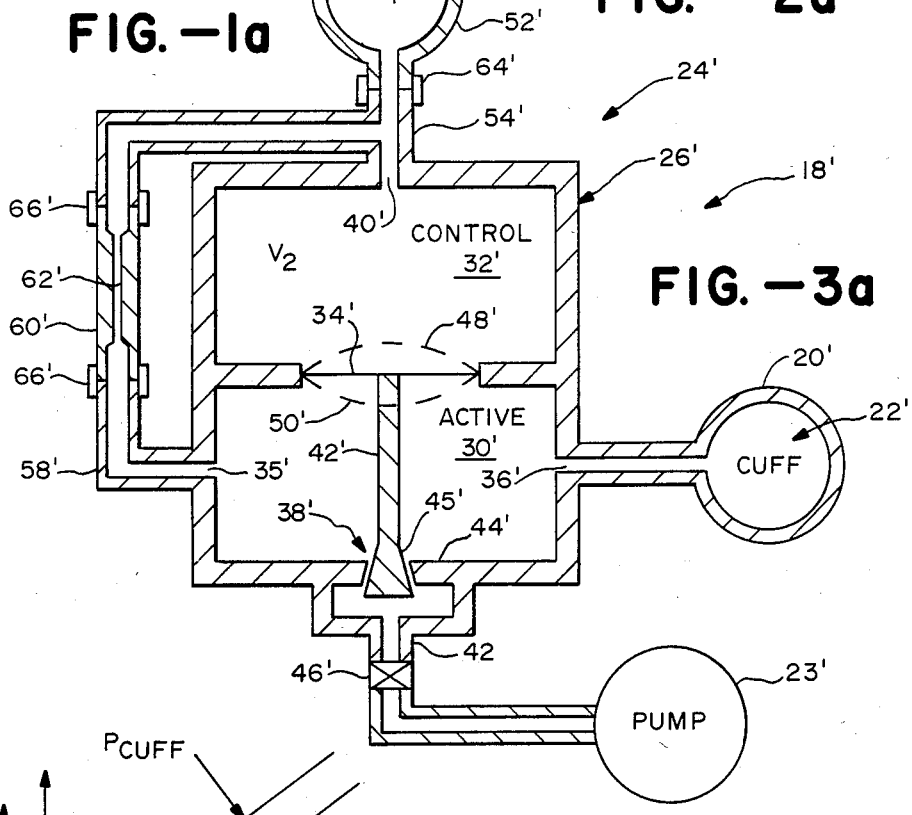
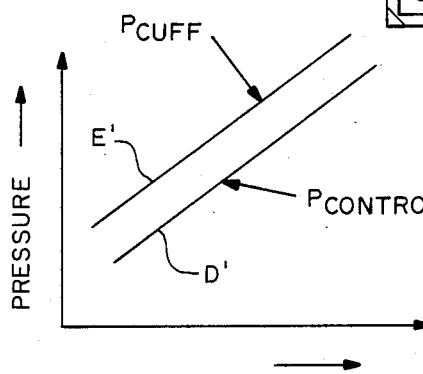

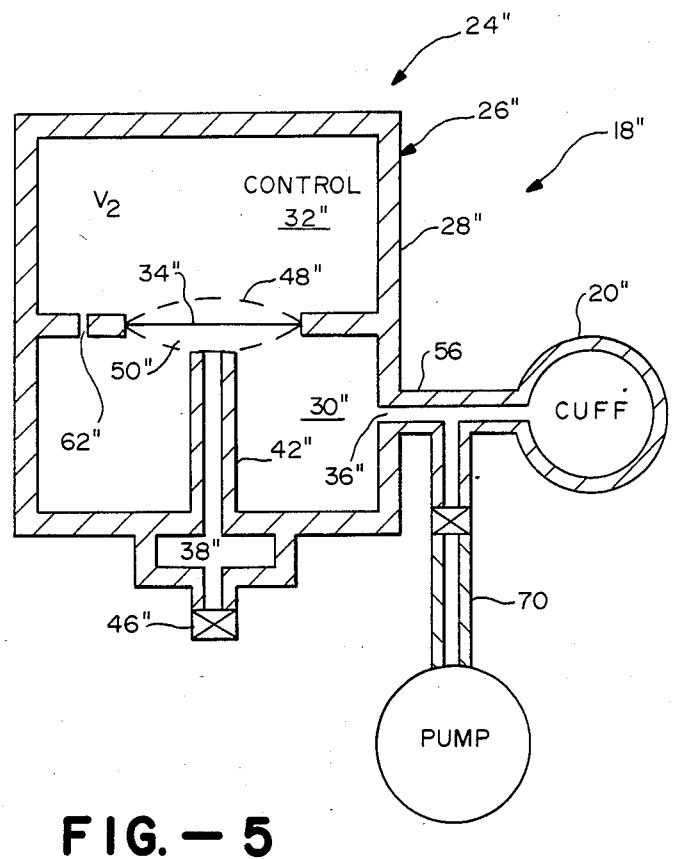
FIG. — 5

4,587,974

LINEAR PRESSURIZING AND DEPRESSURIZING DEVICE

BACKGROUND OF THE INVENTION

The present invention relates generally to a technique for pressurizing and depressurizing a pressurizable container or housing and more particularly to a device which is capable of pressurizing or depressurizing the container or housing in a linear, fixed manner. As will be seen hereinafter, this device is especially suitable for use in an arrangement for taking blood pressure in which a cuff wrapped around the arm or other suitable body part of a patient is first pressurized to a given level and then depressurized sufficient to detect the patient's systolic and diastolic pressures.

Turning briefly to the drawings and specifically FIG. 1, a conventional arrangement for taking blood pressure of a given patient is diagrammatically illustrated and designed by the reference numeral 10. This arrangement includes a standard pressurizable cuff 12 wrapped around the arm 13 (or other suitable body part) of a patient and means generally indicated at 14 for first pressurizing the cuff to a given level above the patient's anticipated systolic pressure and then depressurizing it to a level below the patient's anticipated diastolic pressure. While not shown, the overall arrangement includes suitable means for actually detecting the patient's systolic and diastolic pressures as the cuff is depressurized. For example, in the case of those arrangements which utilized Korotkoff sounds, a stethoscope or a functionally equivalent electronic means may be provided.

In the conventional arrangement described immediately above, once the cuff is pressurized to the desired level and then caused to depressurize, it typically does so in a non-linear, somewhat exponential fashion, as illustrated best in FIG. 2. This Figure graphically illustrates the depressurization of cuff 12 with time for three different sizes of cuffs, a medium size cuff A, a large cuff B and a small cuff C. In each case, the rate of depressurization is greatest in the early stages and then slows down as the pressure within the cuff decreases. As a result, it takes substantially longer to measure the patient's systolic and diastolic pressures then would be case if the cuff could be made to depressurize linearly. Take for example the depressurization ramp (curve) A for a medium cuff. The cuff is initially pressurized to a level above the patients systolic pressure and as it depressurizes, it reaches the systolic pressure S at the time t1 and then the patient's diastolic pressure at the time t3. If the cuff could be made to depressurize linearly, as indicated by the linear ramp (curve) A' the patient's diastolic pressure D would be measured at time t2, substantially earlier than time t3. This time differential between t3 and t2 for standard size arm cuffs is on the order of approximately 10 seconds.

Because arrangement 10 does not depressurize its cuff in a linear fashion but rather exponentially (as described above), it has the disadvantage of being slower than it would be if the cuff could be linearly depressurized. Another disadvantage of the arrangement illustrated relates to the size of cuff 12. Specifically, cuffs of different sizes result in depressurization ramps of different configurations. As illustrated in FIG. 2, the ramp A corresponds to a medium size cuff, the ramp B corresponds to a larger cuff, and the ramp C corresponds to a smaller cuff. Thus, if arrangement 10 includes an electronic means for detecting the patient's systolic and diastolic pressures and if the arrangement uses cuffs of different sizes, suitable circuitry and an adjustment switch would be required to compensate for the different sized cuffs to make the ramps for all cuff sizes approximately equal.

SUMMARY OF THE INVENTION AND OBJECTS

In view of the foregoing, it is a specific object of the present invention to provide an arrangement for taking blood pressure of the general type described in FIG. 1, that is, one in which a cuff wrapped around the arm or other suitable body part of a patient is first pressurized to a given level and the depressurized sufficient to detect the patient's systolic and diastolic pressures, but particularly to an arrangement in which the cuff is depressurized linearly rather than the exponential fashion illustrated in FIG. 2.

Another specific object of the present invention is to provide an arrangement of the last mentioned type in which the cuff is depressurized at the same linear rate regardless of the size of the cuff used.

Still another specific object of the present invention is to provide an arrangement of the last mentioned type in which its cuff is capable of being pressurized at a substantially linear, fixed rate regardless of cuff size.

A further object of the present invention is to provide an arrangement for pressurizing or depressurizing a pressurizable container or housing generally (including but not limited to a blood pressure cuff) at a substantially linear, fixed rate, preferably independent of the volume of the container or housing.

As will be described in more detail hereinafter, a particular "down ramp" device is disclosed herein for depressurizing a blood pressure cuff after the latter has been pressurized to a given level and includes a housing defining adjacent internal active and control pressure chambers separated from one another in an air sealed manner by a diaphragm which moves in a predetermined way within the housing depending upon the differences in pressures within the active and control chambers. The device also includes first means for placing the active and controlled chambers and the cuff in air-flow communication with one another whereby all three thereof are initially pressurized to the given level. Second means cooperating with the diaphragm places the active chamber in air-flow communication with the ambient surroundings only so long as the pressure within the control chamber is greater than the pressure in the active chamber by at most a particular, relatively small amount. In this way, the device forces the cuff to depressurize at a substantially linear, fixed rate, independent of the pressurized volume (e.g. the size) of the cuff.

BRIEF DESCRIPTION OF THE DRAWINGS

The linear down ramp or depressurizing device just described briefly will be described in more detail hereinafter in conjunction with the drawings wherein:

FIG. 1 diagrammatically illustrates a conventional (prior art) arrangement for taking blood pressure, as stated previously;

FIG. 2 graphically illustrates how blood pressure cuffs of different sizes forming part of the arrangement of FIG. 1 depressurize non-linearly, as also stated above;

FIG. 3 diagrammatically illustrates a device especially suitable for use in an arrangement for taking blood pressure and specifically a device designed in accordance with the present invention to cause the cuff forming part of the overall arrangement to be pressurized and then depressurized in a substantially linear, fixed manner independent of the pressurized volume of the cuff; and FIG. 4 graphically illustrates a particular operating feature of the device illustrated in FIG. 3.

Also, as will be described in more detail hereinafter, a particular "up ramp" device is disclosed herein for pressurizing a blood pressure cuff using an appropriate pump and includes a housing defining adjacent internal active and control pressure chambers separated from one another in an air sealed manner by a diaphragm which moves in a predetermined way within the housing depending upon the differences in pressures within the active and control chambers. The device also includes first means for placing the active and controlled chambers and the cuff in air-flow communication with one another whereby all three thereof are initially pressurized to the given level. Second means cooperating with the diaphragm places the active chamber in air-flow communication with the ambient surroundings only so long as the pressure within the control chamber is less than the pressure in the active chamber by a particular, relatively small amount. In this way, the device forces the cuff to pressurize at a substantially linear, fixed rate, dependent of the pressurized volume (e.g. the size) of the cuff or of the pressure applied by the pump.

The up ramp or pressurizing device just described briefly will be described in more detail hereinafter in conjunction with the drawings wherein:

FIG. 1a diagrammatically illustrates a conventional (prior art) arrangement for taking blood pressure;

FIG. 2a graphically illustrates how blood pressure cuffs of different sizes forming part of the arrangement of FIG. 1a pressurize non-linearly;

FIG. 3a diagrammatically illustrates a device especially suitable for use in an arrangement for taking blood pressure and specifically a device designed in accordance with the pressure invention to cause the cuff forming part of the overall arrangement to be pressurized in a substantially linear, fixed manner independent of the pressurized volume of the cuff; and FIG. 4a graphically illustrates a particular operating feature of the device illustrated in FIG. 3.

In addition to the foregoing:

FIG. 5 diagrammatically illustrates a modified arrangement corresponding to the one illustrated in FIG. 3.

DETAILED DESCRIPTION

Turning now to the drawing, attention is immediately directed to FIG. 3 inasmuch as FIGS. 1 and 2 were discussed previously. In FIG. 3, an overall arrangement for taking blood pressure is illustrated and generally designated by the reference numeral 18. This arrangement includes (1) a suitable blood pressure cuff 20 which while not shown is wrapped around the arm of a patient, (2) means 23 including a source of air pressure and a device generally indicated at 24 for pressurizing and depressurizing the cuff, and (3) suitable means (not shown) for detecting the patient's systolic and diastolic blood pressures as cuff 20 is depressurized. This last mentioned means and the cuff itself are readily providable and hence will not be described herein. On the other hand, device 24 is designed in accordance with the present invention to insure that cuff 20 after pressurization thereof is depressurized in a substantially linear, fixed manner, independent of the size of the cuff, that is, its pressurized volume, as will be described in detail below.

Still referring to FIG. 3, device 24 is shown including a diaphragm operated pressure regulator 26 which may be of the general type made available for example by the Air Logic company under product number F4103-25. Regulator 26 is shown including a housing 28 defining adjacent internal pressure chambers, an active chamber 30 and a control chamber 32, separated from one another in an air sealed manner by a flexible diaphragm 34 which moves in a manner to be discussed below in response to differences in pressure within chambers 30 and 32. Housing 28 includes inlet ports 35, 36 and outlet port 38 into and out of chamber 30, respectively, and a control port 40 into chamber 32. A valve stem 42, attached at one end to the diaphragm 34, actuates a valve 45 attached to its other end in response to movements of the diaphragm 34. While a suitable closure valve 46 is shown for opening and closing the flow path through port 38 to the ambient surroundings, this valve functions as a part of the overall device, as will be discussed hereinafter, and does not normally form part of the commercially available pressure regulator.

In order to more fully understand how overall device 24 operates, it is important to understand the way in which regulator 26 functions as a pressure comparator apart from the rest of the device. To this end, let it be assumed that the port 38 is always opened through valve 46. Let it also be assumed that the control chamber 32 is initially at atmospheric (ambient) pressure. Under these circumstances, air (or other fluid) flowing into active chamber 30 through inlet 36 will flow back out of the chamber through outlet port 38. This is because the inflow of air into chamber 30 increases the pressure therein over that of the ambient pressure within chamber 32, so as to cause the diaphragm to stretch away from end 44 of chamber 30, as diagrammatically illustrated by the dotted line 48 and thereby prevent valve 45 from closing port 38. In order to prevent air from escaping chamber 30 through port 38, it is necessary to pressurize chamber 32 to a level sufficiently greater than the pressure within chamber 30 so as to cause diaphragm 34 to stretch in the opposite direction, that is, into chamber 30 sufficient to cause valve 45 to seal port 38, as diagrammatically illustrated by dotted lines 50. Thus, if at any given time the pressure within chamber 30 is at a given level, for example 30 torr, it is necessary to pressurize chamber 32 to a sufficiently greater pressure, for example 33 torr in order to cause the diaphragm to move to its valve closing position. This three torr difference is determined by the stretchability of the diaphragm and may be readily designed into the regulator.

Having briefly described regulator 26 and the way it functions apart from device 24 attention is now directed to the remaining components making up this device. This components include an auxiliary container 52 defining an internal auxiliary chamber 53 having a fixed volume V1 and an array of tubes including (1) a tubular assembly 54 for placing control chamber 32 in fluid communication with auxiliary chamber 53, (2) tubular assembly 56 for placing chamber 30 in fluid communication with the interior of cuff 20, and (3) a tubular assembly 58 for placing the chambers 30 and 32 in fluid communication with one another (with the aid of assembly 54). A flow construction arrangement or pneumatic resistor 60 forms part of tubular assembly 58 and includes a constructed passageway 62 in the flow path between chambers 30 and 32. For reasons to be discussed hereinafter, both the auxiliary container 52 and the flow constriction member 60 are removably connected into their respective operating positions illustrated in FIG. 3. To this end, suitable coupling means generally indicated at 64 and 66 are provided.

Device 24 operates in the following manner to cause cuff 20 to depressurize in a substantially linear, fixed manner independent of the size of cuff 20, after the cuff has been pressurized to a given level. First, the cuff needs to be pressurized. To this end, previously recited pressurized air supply means 23, is interconnected with the cuff by suitable tubular means 70 through an open/shut valve 71. Since the cuff is in direct fluid communication with both chambers 30 and 32 and auxiliary chamber 53 by means of tubular assemblies 54, 56 and 58, it is necessary to initially pressurize all three of these latter chambers to the desired level along with the cuff. In order to do this it is of course necessary to maintain port 38 closed by suitable means such as the closure valve 46.

Once cuff 20 is pressurized to the desired level (along with the chambers 30, 32 and 53), the cuff can be depressurized by merely opening up port 38 by means of valve 46. This causes air initially to escape to the ambient surroundings from chamber 30, thereby dropping the pressure therein. However, because of diaphragm 34, as soon as the pressure within chamber 30 drops to a predetermined level below the pressure in chamber 32, the diaphragm closes port 38. At the same time, air from chambers 32 and 53 and from cuff 20 enter chamber 30 through inlet ports 35 and 36 respectively, thereby increasing the pressure within chamber 30 sufficient to force the diaphragm away from port 38 for opening the latter. Thus, diaphragm 34 may continue to open and close tube 42 to depressurize chambers 30, 32 and 53 and cuff 20. More frequently diaphragm 34 hovers in such a position as to maintain exactly equal the rates of pressure drop in chambers 32 and 53 on the one hand and chamber 30 and cuff 20 on the other hand. As it does so, the pressure differential between chambers 30 and 32 will remain at a fixed level depending upon the stretch characteristics of the diaphragm, for example the three torr pressure value discussed previously. This fixed pressure differential appears across constricted passageway 62 at all times. This means that the flow rate through the constricted passageway in the direction of port 35 is constant at all times. Since the flow rate through the constricted passageway is constant, the pressure within compartments 32 and 53 must drop at a constant or fixed rate, that is, a linear rate.

Since the chamber 32 drops in pressure at a linear rate as described above, the pressure in chamber 30 must also drop at the same linear rate (e.g. following the drop in pressure in chamber 32 by a fixed amount, for example the 3 torr value mentioned above). This is best exemplified in FIG. 4 which graphically illustrates a curve D corresponding to the linear drop in pressure in chamber 32 and a curve E which corresponds to the linear drop in pressure in chamber 30. Note that curve E has the same slope as curve D but always follows curve D by a constant amount which is determined by the stretchability characteristics of diaphragm 34, for example the three torr level mentioned above. Since chamber 30 drops in pressure linearly, so will cuff 20 since it is in fluid communication with this latter chamber. This, device 24 causes cuff 20 to depressurize in the linear manner illustrated by curve E in FIG. 4. The actual change in pressure with time or ramp rate (dP/dt) is governed by the following equation:

$$dP/dt = \frac{\Delta P \cdot P_o}{(V_1 + V_2) \cdot R} \quad (1)$$

Where $P_o$ is equal to an average pressure (about 760 torr); $V_1$ and $V_2$ respectively equal the volumes in chambers 53 and 32; $\Delta P$ equals a fixed constant depending upon the stretchability characteristics of the diaphragm, for example 3 torr; and R is a constant air resistant factor (functionally equivalent to electrical resistance) depending upon the cross section of constricted passageway 62. Thus, in an actual embodiment, if $V_1$ plus $V_2$ is approximately equal to 30 cubic centimeters, if $\Delta P$ equals 3 torr and if R equals 12 Torr sec $cm^{-3}$ (corresponding to about a 10 mil diameter hole), then dP/dt is approximately equal to 6 Torr per second.

It should be noted that the equation for dP/dt above is independent of the volume of cuff 20. Therefore, the rate of depressurization of cuff 20 by means of device 24 is independent of the volume of cuff 20 which means that the device will cause different sized cuffs to depressurize in the same way. This, in turn, means that the overall arrangement does not have to concern itself with the size of the cuff being depressurized. At the same time, the ramp rate dP/dt of device 24 can be varied by changing $V_1$, $V_2$ and/or R. It is impractical to change the volume $V_2$. Therefore, the most practical means of varying the ramp rate is to vary the volume $V_1$ by using different containers 52 of different volumes or by varying the pneumatic resistance R indicated at 60 in FIG. 3. By increasing the volume $V_1$, the slope of curve E is decreased and vice versa. Couplings 64, 66 are used to provide different containers and/or pneumatic resistors.

From the foregoing discussion, it should be apparent that device 24 can be used to depressurize cuff 20 at a substantially linear, constant rate, independent of the size of the cuff. It should be equally apparent that device 24 can be utilized with pressurizable containers or housings other than a blood pressure cuff for depressurizing these other containers and housings at substantially linear, fixed rates, independent of the size of these latter containers or housings. For example, device 24 could be used to pressurize and then depressurize a pneumatic accumulator.

Referring now to FIGS. 1a and 2a there is illustrated the same type of blood pressure measurement arrangement as above illustrated in FIGS. 1 and 2 with the exception that the pressure in the blood pressure cuff is designed to ramp upward instead of downward. Thus an arrangement 10' using a cuff 12' positioned around the arm 13' of a patient is shown in FIG. 1a along the means 14' for first pressurizing and then depressurizing the cuff. FIG. 2a shows exponential pressurizing curves A', B', C' corresponding to medium, large and small cuffs and cuff A'' corresponding to a linear pressurization curve which illustrates that it would be faster to pressurize linearly than exponentially.

In FIG. 3a, an overall arrangement for taking blood pressure is illustrated and generally designated by the reference numeral 18'. This arrangement includes (1) a suitable blood pressure cuff 20' shown wrapped around the arm of a patient, (2) means 23' including a source of air pressure and a device generally indicated at 24' for pressurizing the cuff, and (3) suitable means (not shown) for detecting the patient's systolic and diastolic blood pressures as cuff 20' is pressurized. This last mentioned means and the cuff itself are readily providable and hence will not be described herein. On the other hand, device 24' is designed in accordance with the present invention to insure that cuff 20' is pressurized in a substantially linear, fixed manner, independent of the size of the cuff, that is, its pressurized volume as will be described in detail below.

Still referring to FIG. 3a, device 24' is shown including a diaphragm operated pressure regulator 26'. Regulator 26' is shown including a housing 28' defining adjacent internal pressure chambers, an active chamber 30' and a control chamber 32', separated from one another in an air sealed manner by a flexible diaphragm 34' which moves in a manner to be discussed below in response to differences in pressure within chambers 30' and 32'. Housing 28' includes inlet ports 35', 36' and outlet port 38' into and out of chamber 30', respectively, and a control port 40' into chamber 32'. A valve stem 42', attached at one end to the diaphragm 34', actuates a valve 45' attached to its other end in response to movements of the diaphragm 34'. While a suitable closure valve 46' is shown for opening and closing the flow path into chamber 32' through port 38', this valve functions as a part of the overall device, as will be discussed hereinafter, and does not normally form part of the commercially available pressure regulator.

In order to more fully understand how overall device 24' operates, it is important to understand the way in which regulator 26' functions as a pressure comparator apart from the rest of the device. To this end, let it be assumed that valve 46' is always opened. Let is also be assumed that the control chamber 32' is initially at atmospheric (ambient) pressure. It should also be pointed out that the relaxed position or set of diaphragm 34' is shown as a solid line at 34'. Under these circumstances, air (or other fluid) flowing cannot freely flow into active chamber 30' through port 38' (ignoring for the moment that the pump is connected thereto). This is because any inflow of air into chamber 30' increases the pressure therein over that of the ambient pressure within chamber 32', so as to cause the diaphragm to stretch away from chamber 30', as diagrammatically illustrated by the dotted line 48' and thereby close port 38'. To allow air to pass into chamber 30' through port 38', it is necessary to pressurize chamber 32' to a sufficient level as compared to the pressure within chamber 30' so as to cause diaphragm 34' to relax or stretch in the opposite direction, that is, in the direction of chamber 30' sufficient to open port 38' as diagrammatically illustrated by dotted lines 50'. Thus, if at any given time the pressure within chamber 30' is at a given level, for example 30 torr, it is necessary to pressurize chamber 32' to a sufficient pressure, for example 27 torr in order to cause the diaphragm to move to its valve opening position. This three torr difference is determined by the stretchability and the designed set of the diaphragm and may be readily designed into the regulator.

Having briefly described regulator 28' and the way it functions apart from device 24' attention is now directed to the remaining components making up this device. These components include an auxiliary container 52' defining an internal auxiliary chamber 53' having a fixed volume V1 and an array of tubes including (1) a tubular assembly 54' for placing control chamber 32' in fluid communication with auxiliary chamber 53', (2) tubular assembly 56' for placing chamber 30' in fluid communication with the interior of cuff 20', and (3) a tubular assembly 58' for placing the chambers 30' and 32' in fluid communication with one another (with the aid of assembly 54'). An additional tubular assembly 70' places pump 23' in fluid communication with port 38' through valve 46'. A flow constriction arrangement or pneumatic resistor 60' forms part of tubular assembly 58' and includes a constricted passageway 62' in the flow path between chambers 30' and 32'. For the reasons discussed previously with respect to FIG. 3 both the auxiliary container 52' and the flow constriction member 60' are removably connected into their respective operating positions illustrated in FIG. 3a. To this end, suitable coupling means generally indicated at 64' and 66' are provided.

Device 24' operates in the following manner to cause cuff 20' to pressurize in a substantially linear, fixed manner independent of the size of cuff 20'. First, the pressurizing means 23' is turned on. The cuff can then be pressurized by merely opening up tubular assembly 70' by means of valve 46'. This causes limited air initially to pass into chamber 30', thereby increasing the pressure therein. However, because of diaphragm 34', as soon as the pressure within chamber 30' increases to a predetermined level above the pressure in chamber 32', the diaphragm closes port 38'. At the same time, air enters chambers 32' and 53' from cuff 20' and chamber 30' through tubular assemblies 58' and 54', thereby increasing the pressure within chamber 32' sufficient to force the diaphragm toward chamber 30' thus opening port 38' again. Thus, diaphragm 34' continues to open and close port 38' to pressurize chambers 30', 32' and 53' and cuff 20'. More frequently diaphragm 34' hovers in such a position as to maintain exactly equal the rates of pressure rise in chambers 32' and 53' on the one hand and chamber 30' and cuff 20' on the other. As it does so, the pressure differential between chambers 30' and 32' will remain at a fixed level depending upon the stretch characteristics and the set of the diaphragm, for example the three torr pressure value discussed previously. This fixed pressure differential appears across constricted passageway 60 at all times. This means that the flow rate through the constricted passageway in the direction of port 40' is constant at all times. Since the flow rate through the constricted passageway is constant, the pressure within compartments 32' and 53' must rise at a constant or fixed rate, that is, a linear rate. Since the chamber 32' rises in pressure at a linear rate, the pressure in chamber 30' must also rise at the same linear rate (e.g. preceding the rise in pressure in chamber 32' by a fixed amount, for example the 3 torr value mentioned above). This is best exemplified in FIG. 4a which graphically illustrates a curve D' corresponding to the linear rise in pressure in chamber 32' and a curve E' which corresponds to the linear rise in pressure in chamber 30'. Note that curve D' has the same slope as curve E' but always follows curve E' by a constant amount which is determined by the stretchability and set characteristics of diaphragm 34', for example the three torr level mentioned above. Since chamber 30' rises in pressure linearly, so will cuff 20' since it is in fluid communication with this latter chamber. Thus, device 24' causes cuff 20' to pressurize in the linear manner illustrated by curve E' in FIG. 4a. The actual change in pressure with time or ramp rate (dP/dt) is governed by the following equation:

$$dP/dt = \frac{\Delta P \cdot P_o}{(V_1 + V_2) \cdot R} \quad (2)$$

Where $P_o$ is equal to an average pressure (about 760 torr); $V_1$ and $V_2$ respectively equal the volumes in chambers 53' and 32'; $\Delta P$ equals a fixed constant depending upon the stretchability characteristics of the diaphragm, for example 3 torr; and R is a constant air resistant factor (functionally equivalent to electrical resistance) depending upon the cross section of constricted passageway 62'. Thus, in an actual embodiment, if $V_1$ plus $V_2$ is approximately equal to 30 cubic centimeters, if $\Delta P$ equals 3 torr and if R equals 12 Torr sec cm$^{-3}$ (corresponding to about a 10 mil diameter hole), then dP/dt is approximately equal to 6 Torr per second.

It should be noted that the equation (2) for dP/dt above is independent of the volume of cuff 20'. Therefore, the rate of pressurization of cuff 20' by means of device 24' is independent of the volume of cuff 20' which means that the device will cause different sized cuffs to pressurize in the same way. This, in turn, means that the overall arrangement does not have to concern itself with the size of the cuff being pressurized. At the same time, the ramp rate dP/dt of device 24' can be varied by changing $V_1$, $V_2$ and/or R. It is impractical to change the volume $V_2$. Therefore, the most practical means of varying the ramp rate is to vary the volume $V_1$ by using different containers 52' of different volumes or by varying the pneumatic resistance R indicated at 60' in FIG. 3a. By increasing the volume $V_1$, the slope of curve E is decreased and vice versa.

From the foregoing discussion, it should be apparent that device 24' can be used to pressurize cuff 20' at a substantially linear, constant rate, independent of the size of the cuff. It should be equally apparent that device 24 can be utilized with pressurizable containers or housings other than a blood pressure cuff for pressurizing these other containers and housings at substantially linear, fixed rates, independent of the size of these latter containers or housings. For example, device 24' could be used to pressurize or depressurize a pneumatic accumulator.

Turning now to FIG. 5, an arrangement for taking blood pressure is illustrated and generally designated by the reference 18". This arrangement is a simplified and preferred version of arrangement 18 illustrated in FIG. 3 and includes a number of components corresponding to arrangement 18. For example, the arrangement 18' includes the same blood pressure cuff 20, the same means 23 including a source of air pressure and suitable means not shown for detecting the patient's systolic and diastolic blood pressures. Arrangement 18" also includes a device 24" which corresponds to previously described device 24 but which is the simplified version thereof.

Device 24", like device 24 includes a diaphragm operated pressure regulator 26" having the same type of housing 28" defining adjacent internal pressure chambers, and active chamber 30" and a control chamber 32", separated from one another in an air sealed manner by a flexible diaphragm 34" which moves in the same manner as previously described diaphragm 34. Device 24" also includes inlet and outlet ports 36" and 38" corresponding to ports 36 and 38 and a tubular assembly 56 which connects the cuff and pump means to inlet port 36". However, the device 24" differs from device 24 in that it does not include a separate container 52 and associated tubular assemblies and port or external resistor, although it could. It does however have an internal resistor 62" corresponding to pneumatic resistor 62 extending between the chambers 30" and 32". In addition, rather than a stem type of valve, device 24" includes a tubular member 42" defining port 38" and having an opened top end positioned directly below the diaphragm 34". This diaphragm operates to open and close the passageway through tube 42" in the same manner as diaphragm 34 operates to open and close port 38 by means of stem valve 45. In addition, port 38" is opened and closed by means of valve 46 also.

Overall arrangement 18" operates in the same manner as previously described arrangement 18, based on equation (1), to provide linear depressurization of cuff 20", except that there is no $V_2$ in the equation. In this latter regard, device 24" could be readily modified to include the container 52 defining a chamber 53 of volume V1 and an external constriction 62 rather than an internal one. In fact, this modified arrangement would be identical to the one illustrated in FIG. 3, except for the use of the tubular member 42" rather than stem 42 and valve 45.

What is claimed is:

1. In an arrangement for taking blood pressure in which a cuff wrapped around a body part of a patient is first pressurized to a given level and then depressurized sufficient to detect the patient's systolic and diastolic pressures, the improvement comprising means acting on said cuff after the latter has been pressurized to said given level for causing it to depressurize in a substantially linear way independent of the pressurized volume of the cuff, said depressurizing means including; a housing defining adjacent internal active and control pressure chambers separated from one another in an air sealed manner by a diaphragm; first means for placing said active and control chambers and said cuff in air-flow communication with one another whereby all three thereof are initially pressurized to said given level; and second means cooperating with said diaphragm for placing said active chamber in air-flow communication with the ambient surroundings only as long as the pressure within said control chamber is at most greater than the pressure in said active chamber by a particular relatively small amount, said second means closing the air flow communication between said active chamber and ambient surroundings if the pressure within said control chamber is greater than the pressure with said active chamber by more than said particular amount.

2. The improvement according to claim 1 wherein said particular relatively small amount of pressure is on the order of 3 torr.

3. The improvement according to claim 1 wherein said depressurizing means includes means for changing the way in which said cuff is linearly depressurized.

4. The improvement according to claim 3 wherein said changing means includes means for changing the effective volume of said control chamber whereby the manner in which said cuff is linearly depressurized changes as a function thereof.

5. The improvement according to claim 4 wherein said volume changing means includes means for placing one of a plurality of different auxiliary chambers of varying sized in air-flow communication with said control chamber whereby the effective volume of said control chamber can be changed by changing the size of said auxiliary chamber.

6. In an arrangement for taking blood pressure in which a cuff wrapped around a body part of a patient is first pressurized to a given level and then depressurized sufficient to detect the patient's systolic and diastolic pressures, a device configured to cooperate with said cuff for causing the latter to depressurize after it has been pressurized to a given level in a substantially linear, fixed manner independent of the pressurized volume of the cuff, said device comprising:

(a) a housing defining adjacent internal active and control pressure chambers separated from one another in an air sealed manner by a diaphragm which is movable within said housing in predetermined ways responsive to the differences in pressure within said active and control chambers;

(b) an auxiliary container of fixed volume;

(c) an assembly of tubular means including a first tubular means for placing said control chamber and said auxiliary container in fluid communication with another, a second tubular means for placing said active chamber and said cuff in fluid communication with one another, and third tubular means for placing said active and control chambers in fluid communication with one another, said third tubular means including a flow constriction device having a constricted flow passage in the flow path between said chambers; and (d) a separate tubular means extending through said housing between said active chamber and the ambient surroundings and cooperating with said diaphragm for placing said active chamber in air-flow communication with the ambient surroundings only so long as the pressure within said control chamber is at most greater than the pressure in said active chamber by a particular relatively small amount, said separate tubular means closing the air flow communication between said active chamber and ambient surroundings if the pressure within said control chamber is greater than the pressure within said active chamber by more than said particular amount, whereby the overall arrangement acts on said cuff, causing the latter to depressurize after it has been pressurized to a given level in a substantially linear, fixed manner independent of the pressurized volume of the cuff.

7. An arrangement comprising means acting on a container after the latter has been pressurized to a given level for causing it to depressurize in a substantially linear fixed manner, said depressurizing means including: a housing defining adjacent internal active and control pressure chambers separated from one another in an air sealed manner by a diaphragm; first means for placing said active and control chambers and said container in air-flow communication with one another whereby all three thereof are initially pressurized to said given level; and second means cooperating with said diaphragm for placing said active chamber in air-flow communication with the ambient surroundings only as long as the pressure within said control chamber is at most greater than the pressure in said active chamber by a particular relatively small amount, said second means closing the air flow communication between said active chamber and ambient surroundings if the pressure within said control chamber is greater than the pressure within said active chamber by more than said particular amount.

8. In an arrangement for taking blood pressure in which a cuff wrapped around a body part of a patient is first pressurized to a given level and then depressurized sufficient to detect the patient's systolic and diastolic pressures, the improvement comprising means for pressurizing said cuff to said given level in a substantially linear, fixed manner, said pressurizing means including: a housing defining adjacent internal active and control pressure chambers separated from one another in an air sealed manner by a diaphragm; first means for placing said active and control chambers and said cuff in air-flow communication with one another whereby all three thereof are initially maintained at ambient pressure; and second means cooperating with said diaphragm for placing said active chamber in air-flow communication with a pump only as long as the pressure within said active chamber is at most greater than the pressure in said control chamber by a particular relatively small amount, said second closing the air flow communication between said active chamber and said pump means if the pressure within said active chamber is greater than the pressure within said control chamber by more than said particular amount.

9. An arrangement comprising means for pressurizing a container in a substantially linear fixed manner, said pressurizing means including: a housing defining adjacent internal active and control pressure chambers separated from one another in an air sealed manner by a diaphragm; first means for placing said active and control chambers and said container in air-flow communication with one another whereby all three thereof are initially maintained at ambient pressure; and second means cooperating with said diaphragm for placing said active chamber in air-flow communication with a pump only as long as the pressure within said active chamber is at most greater than the pressure in said control chamber by a particular relatively small amount, said second means closing the air-flow communication between said active chamber and said pump if the pressure within said active chamber is greater than the pressure within said control chamber by more than said particular amount.

10. In an arrangement for taking blood pressure in which a cuff wrapped around a body part of a patient is first pressurized to a given level and then depressurized sufficient to detect the patient's systolic and diastolic pressures, a device configured to cooperate with said cuff for causing the latter to depressurize after it has been pressurized to a given level in a substantially linear, fixed manner independent of the pressurized volume of the cuff, said device comprising:

(a) a housing defining adjacent internal active and control pressure chambers separated from one another in an air sealed manner by a diaphragm which is movable within said housing in predetermined ways responsive to the differences in pressure within said active and control chambers;

(b) means for placing said active chamber and said cuff in fluid communication with one another;

(c) means for placing said active and control chambers in fluid communication with one another, said last-mentioned means including a constricted flow passage in the flow path between said chambers; and (d) means cooperating with said diaphragm for placing said active chamber in air-flow communication with the ambient surroundings only so long as the pressure within said control chamber is at most greater than the pressure in said active chamber by a particular relatively small amount, said last-mentioned means closing air flow communication between said active chamber and ambient surroundings if the pressure within said control chamber is greater than the pressure within said active chamber by more than said particular amount, whereby the overall arrangement acts on said cuff for causing the latter to depressurize after it has ben pressurized to a given level in a substantially linear, fixed manner independent of the pressurized volume of the cuff.

11. In an arrangement for taking blood pressure in which a cuff wrapped around a body part of a patient is first pressurized to a given level and then depressurized sufficient to detect the patient's systolic and diastolic pressures, a device configured to cooperate with said cuff for causing the latter to pressurize to a given level in a substantially linear, fixed manner independent of the pressurized volume of the cuff, said device comprising:

(a) a housing defining adjacent internal active and control pressure chambers separated from one another in an air sealed manner by a diaphragm which is movable within said housing in predetermined ways responsive to the differences in pressure within said active and control chambers;

(b) an auxiliary container of fixed volume;

(c) an assembly of tubular means including a first tubular means for placing said control chamber and said auxiliary container in fluid communication with another, a second tubular means for placing said active chamber and said cuff in fluid communication with one another and third tubular means for placing said active and control chambers in fluid communication with one another, said third tubular means including a flow constriction device having a constricted flow passage in the flow path between said chambers; and (d) means cooperating with said diaphragm for placing said active chamber in air-flow communication with a pump only so long as the pressure within said active chamber is at most greater than the pressure in said control chamber by a particular relatively small amount, said last-mentioned means closing air flow communication between said active chamber and said pump if the pressure within said active chamber is greater than the pressure within said control chamber by more than said particular amount, whereby the overall arrangement acts on said cuff for causing the latter to pressurize in a substantially linear, fixed manner independent of the pressurized volume of the cuff.

12. In an arrangement for taking blood pressure in which a cuff wrapped around a body part of a patient is first pressurized to a given level and then depressurized sufficient to detect the patient's systolic and diastolic pressures, a device configured to cooperate with said cuff for causing the latter to pressurize to a given level in a substantially linear, fixed manner independent of the pressurized volume of the cuff, said device comprising:

(a) a housing defining adjacent internal active and control pressure chambers separated from one another in an air sealed manner by a diaphragm which is movable within sealed housing in predetermined ways responsive to the differences in pressure within said active and control chambers;

(b) first means for placing said active chamber and said cuff in fluid communication with one another;

(c) means for placing said active and control chambers in fluid communication with one another, said last-mentioned means including a constricted flow passage in the flow path between said chambers; and (d) means cooperating with said diaphragm for placing said active chamber in air-flow communication with a pump only so long as the pressure within said active chamber is at most greater than the pressure in said control chamber by a particular relatively small amount, said last-mentioned closing air flow communication between said active chamber and said pump if the pressure within said active chamber is greater than the pressure within said control chamber by more than said particular amount, whereby the overall arrangement acts on said cuff for causing the latter to pressurize in a substantially linear, fixed manner independent of the pressurized volume of the cuff.

* * * * *

UNITED STATES PATENT AND TRADEMARK OFFICE
CERTIFICATE OF CORRECTION

PATENT NO. : 4,587,974
DATED : May 13, 1986
INVENTOR(S) : William T. Link

It is certified that error appears in the above-identified patent and that said Letters Patent is hereby corrected as shown below:

Column 1, line 45, change "then" to --than--;
        line 46, before "case" insert --the--;
        line 49, change "patients" to --patient's--.

Column 2, line 15, change "the" to --then--.

Column 3, line 44, change "pressure" to --present--.

Column 4, line 59, change "26" to --28--;
        line 62, change "This" to --These--.

Column 12, line 21, after "second" insert --means--;
         line 23, after "pump" delete "means".

Column 13, line 11, change "ben" to --been--.

Column 14, line 22, change "sealed" to --said--.

Signed and Sealed this

Seventh Day of October, 1986

[SEAL]

*Attest:*

DONALD J. QUIGG

*Attesting Officer*      *Commissioner of Patents and Trademarks*